United States Patent [19]

Van Der Jagt

[11] Patent Number: Plant 6,079

[45] Date of Patent: Jan. 5, 1988

[54] CHRYSANTHEMUM NAMED 'YELLOW REPIN'

[75] Inventor: Martinus Van Der Jagt, Ter Aar, Netherlands

[73] Assignee: Chrysanthemum Breeders Association NV, Netherlands Antilles

[21] Appl. No.: 772,185

[22] Filed: Sep. 3, 1985

Related U.S. Application Data

[63] Continuation of Ser. No. 623,096, Jun. 21, 1984.

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Parkhurst & Oliff

[57] ABSTRACT

The present invention is a new and distinct variety of Chrysanthemum with a medium size bloom and Indian yellow color.

3 Drawing Figures

This is a continuation of application Ser. No. 623,096, filed June 21, 1984.

BACKGROUND OF THE INVENTION

The present invention comprises a new and distinct cultivar of Chrysanthemum plant which is a cross of unknown parents. The invention was discovered by Martinus Van Der Jagt in March, 1982 at Ter Aar, Holland. The invention has been asexually reproduced by cuttings at the same location. The new cultivar has been found to retain its distinctive characteristics through successive propagations.

BRIEF DESCRIPTION OF THE DRAWINGS

The present invention of a new and distinct variety of Chrysanthemum is shown in the accompanying drawings, the color being as nearly true as possible with color photographs of this type.

Sheets 1 and 2 show various stages of bloom of the new cultivar.

Sheet 3 shows the foliage and stem of the new cultivar.

DESCRIPTION OF THE INVENTION

This new variety of Chrysanthemum is of the botanical classification *Chrysanthemum morifolium*, named 'Yellow Repin'. When grown in the vicinity of Ter Aar, Holland, it has a response time of approximately 9 weeks. This new variety produces medium sized bright Indian yellow blooms with a green yellow center having a three week permanence. This new variety of Chrysanthemum has been found to retain its distinctive characteristics throughout successive propagations and may be grown year round under greenhouse conditions.

The following is a description of the plant and characteristics that distinguish it over related known varieties and its antecedants:

Bud:
- *Size.*—Medium.
- *Form.*—Flat top.
- *Color.*—Indian yellow (RHS 6/1).

Botanical classification: *Chrysanthemum morifolium.*

Bloom:
- *Size.*—Medium.
- *Fully expanded.*—7–9 cm.
- *Borne.*—Single, sometimes several.

- *Stems.*—Strong.
- *Form.*—Single.
- *Permanence.*—3 weeks.

Color:
- *Center of flower.*—Willow Green RHS 000862+Cadmium orange 8.
- *Base of petals.*—Indian yellow RHS 6/1.
- *Inside of petals.*—Indian yellow RHS 6/1.
- *Reverse of petals.*—Indian yellow RHS 6/1.
- *Outer petals.*—Indian yellow RHS 6/1.
- *Tonality from a distance.*—Yellow single, well filled. A rather big center.

Discoloration: I
- *Beginning to maturity.*—Buttercup yellow RHS 5/1 to Indian yellow (RHS 6/1).
- *Maturity.*—The flower keeps its color.

Petals:
- *Texture.*—Rough.
- *Number.*—35–37.
- *Arrangement.*—Well imbricated.
- *Persistance.*—Normal. Petals keep straight.
- *Fragrance.*—Chrysanthemum.

Re productive organs:
- *Stamens.*—Normal.
- *Pollen.*—Appears in normal quantity.
- *Styles.*—Columnar.
- *Length.*—Medium.
- *Stigmas.*—Medium yellow.
- *Ovaries.*—Enclosed in calyx.

Plant:
- *Form.*—Herbaceous.
- *Growth.*—Vigorous.
- *Height.*—Tall.
- *Peduncle.*—Strong.

Foliage:
- *Color.*—Dark green.
- *Size.*—Medium to large.
- *Quantity.*—Normal.
- *Shape.*—Pointed.
- *Texture.*—Normal.
- *Ribs and veins.*—Ordinary.
- *Edge.*—Deeply undulated.
- *Leaf underside.*—Smooth.
- *Upperside.*—Smooth.

In the description above color references are made to the "Horticultural Color Chart I & II" issued by the Britisch Colour Council in collaboration with The Royal Horticultural Society, Copyright Robert F. Wilson, Vol. I, 1938; Vol. II, 1941, printed by Henry Stone and Son, Ltd. Banbury, England.

I claim:

1. A new and distinctive variety of Chrysanthemum named 'Yellow Repin', as described and illustrated in the foregoing specification and accompanying drawings.

* * * * *

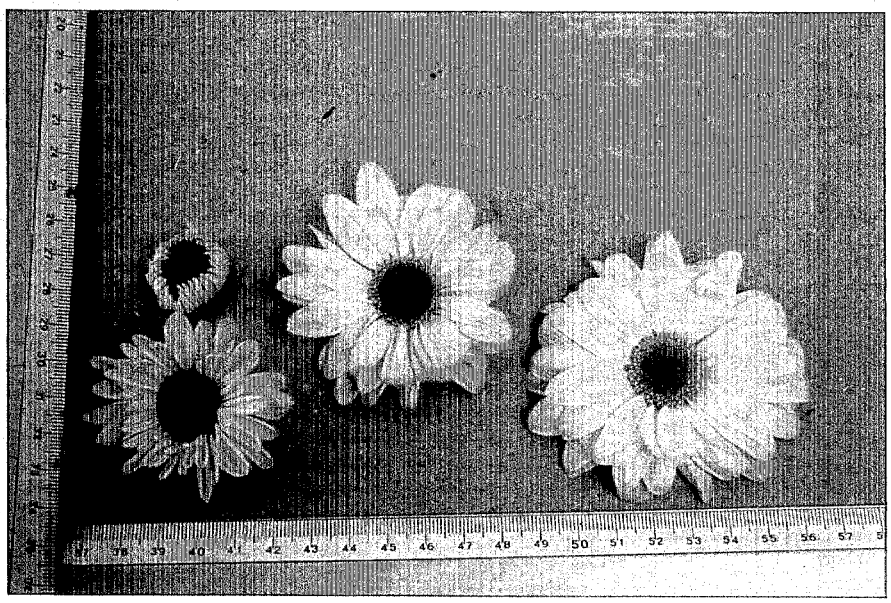

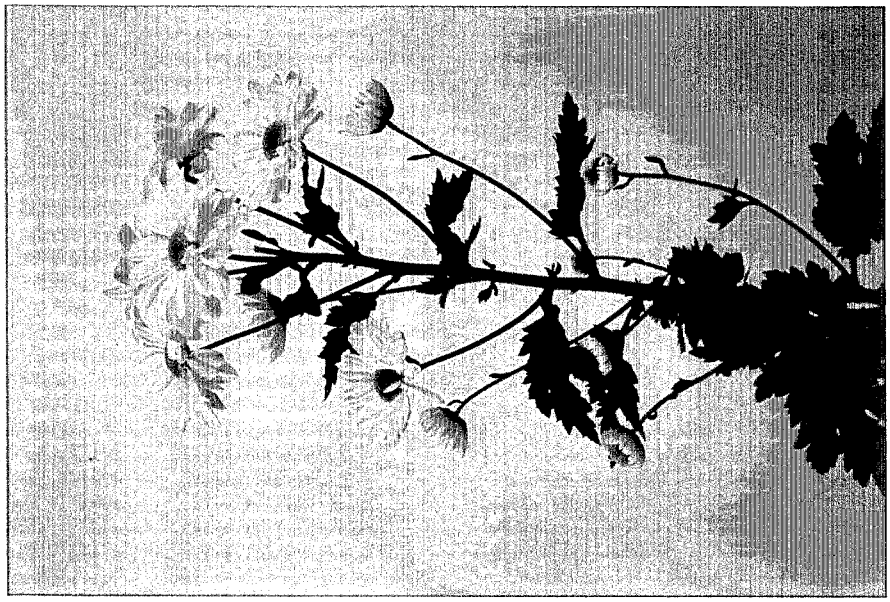
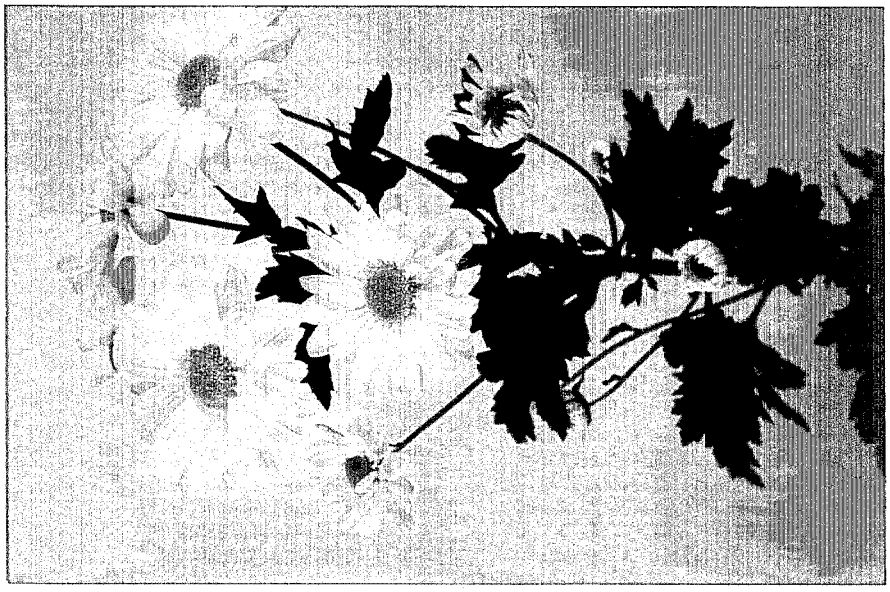

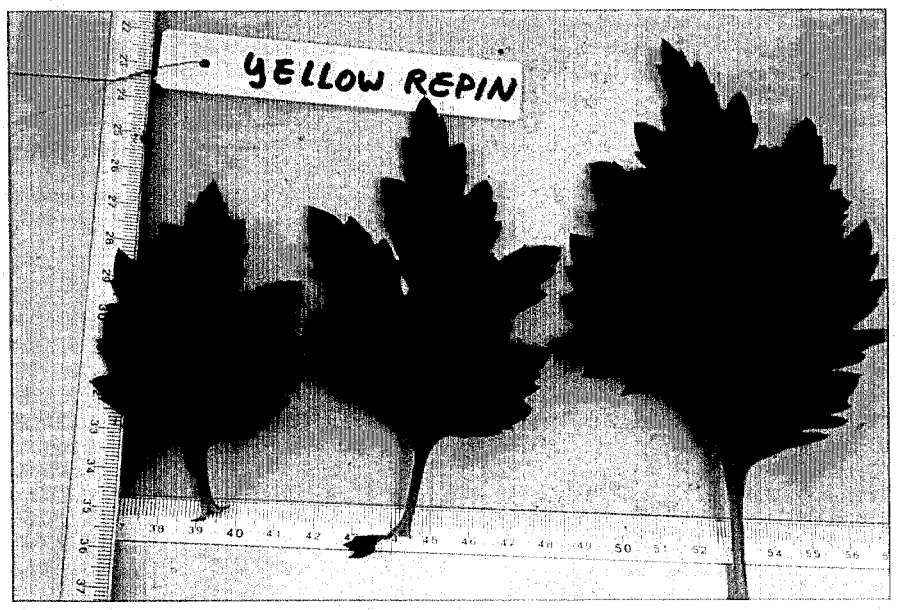
YELLOW REPIN
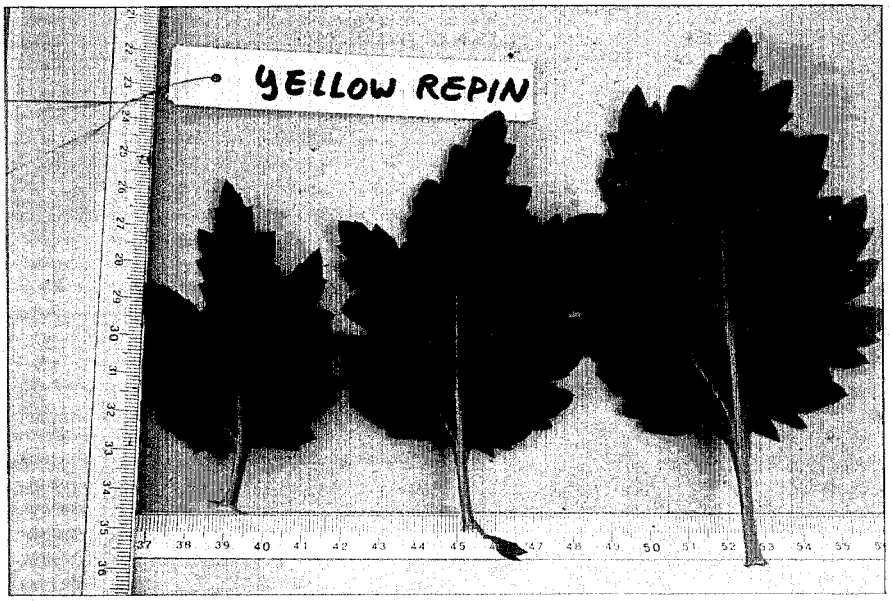
YELLOW REPIN